United States Patent
Sias

(10) Patent No.: US 10,729,318 B2
(45) Date of Patent: Aug. 4, 2020

(54) ANOSCOPE

(71) Applicant: Francesco Sias, Cagliari (IT)

(72) Inventor: Francesco Sias, Cagliari (IT)

( * ) Notice: Subject to any disclaimer, the term of this patent is extended or adjusted under 35 U.S.C. 154(b) by 404 days.

(21) Appl. No.: 15/625,228

(22) Filed: Jun. 16, 2017

(65) Prior Publication Data

US 2018/0125350 A1    May 10, 2018

(30) Foreign Application Priority Data

Nov. 9, 2016 (IT) .......................... 102016000112850

(51) Int. Cl.
*A61B 1/31* (2006.01)
*A61B 1/00* (2006.01)
(Continued)

(52) U.S. Cl.
CPC .............. *A61B 1/31* (2013.01); *A61B 1/0008* (2013.01); *A61B 1/00177* (2013.01);
(Continued)

(58) Field of Classification Search
CPC ... A61B 2018/005; A61B 1/31; A61B 1/0008; A61B 1/00177; A61B 1/018; A61B 1/0676; A61B 18/1485
See application file for complete search history.

(56) References Cited

U.S. PATENT DOCUMENTS 5,395,368 A * 3/1995 Ellman .................. A61B 18/14
606/45
7,611,458 B2 11/2009 Sias
(Continued)

FOREIGN PATENT DOCUMENTS

| EP | 2692282 B1 | 11/2014 |
|---|---|---|
| RU | 2580903 C1 | 4/2016 |
| WO | 2016203395 A1 | 12/2016 |

*Primary Examiner* — Timothy J Neal
*Assistant Examiner* — Jae Woo
(74) *Attorney, Agent, or Firm* — Laubscher & Laubscher, P.C.

(57) ABSTRACT

An anoscope comprises a graspable portion, arranged for being grasped by an operator, and a body, arranged for being inserted into the terminal tract of the rectum of a patient. A cavity and at least one operating window are made in the body of the anoscope. The anoscope further comprises a housing and a seat, which are comprised in the cavity of the body. The housing is arranged for containing at least one surgical instrument suitable for treating hemorrhoids and the seat is arranged for containing at least one lighting device. A method for treating a hemorrhoid in a patient comprises the following steps: a) Inserting an anoscope into the terminal tract of the rectum of the patient through the anal opening; b) Positioning the body of the anoscope in such a way that an operating window or opening of the anoscope is near a zone of rectal mucosa to be treated, positioned near the hemorrhoids; c) Positioning a surgical instrument suitable for treating hemorrhoids inside the body of the anoscope so as to reach the operating window or opening and, through the operating window or opening, reaching the zone of rectal mucosa to be treated; d) Producing a localized heat in the submucosa of the zone of rectal mucosa to be treated through the surgical instrument, such localized heat being a heat that is limited to the zone of rectal mucosa to be treated; e) Inducing a volume reduction of the hemorrhoid as a result of the localized heat produced.

20 Claims, 8 Drawing Sheets

(51) Int. Cl.
  *A61B 18/14* (2006.01)
  *A61B 18/20* (2006.01)
  *A61B 1/32* (2006.01)
  *A61B 1/06* (2006.01)
  *A61B 1/018* (2006.01)
  *A61B 17/34* (2006.01)
  *A61B 18/00* (2006.01)
  *A61B 18/22* (2006.01)

(52) U.S. Cl.
  CPC ............ *A61B 1/018* (2013.01); *A61B 1/0676* (2013.01); *A61B 1/0684* (2013.01); *A61B 1/32* (2013.01); *A61B 18/1485* (2013.01); *A61B 18/20* (2013.01); *A61B 1/00073* (2013.01); *A61B 18/22* (2013.01); *A61B 2017/3452* (2013.01); *A61B 2018/005* (2013.01); *A61B 2018/00601* (2013.01); *A61B 2018/00982* (2013.01); *A61B 2018/00994* (2013.01); *A61B 2018/1412* (2013.01)

(56) References Cited

U.S. PATENT DOCUMENTS

| | | | | |
|---|---|---|---|---|
| 9,332,898 | B2* | 5/2016 | McMahon | A61B 1/00105 |
| 9,615,847 | B2* | 4/2017 | Kirkemo | A61B 17/3478 |
| 9,724,124 | B2* | 8/2017 | Li | A61B 17/3403 |
| 10,463,244 | B2* | 11/2019 | Bastia | A61B 1/00128 |
| 2004/0034339 | A1* | 2/2004 | Stoller | A61B 1/3132 606/1 |
| 2005/0234299 | A1* | 10/2005 | Eitenmuller | A61B 1/00177 600/160 |
| 2006/0009797 | A1* | 1/2006 | Armstrong | A61B 1/00071 606/197 |
| 2006/0036129 | A1* | 2/2006 | Sias | A61B 1/31 600/135 |
| 2006/0155169 | A1* | 7/2006 | Bastia | A61B 1/00105 600/199 |
| 2006/0167473 | A1* | 7/2006 | Scheyer | A61B 1/00177 606/139 |
| 2007/0093692 | A1* | 4/2007 | Leroy | A61B 1/0607 600/182 |
| 2007/0197958 | A1* | 8/2007 | Hern | A61B 1/31 604/73 |
| 2007/0230167 | A1* | 10/2007 | McMahon | A61B 1/303 362/157 |
| 2008/0228038 | A1* | 9/2008 | McMahon | A61B 1/00105 600/223 |
| 2008/0281204 | A1* | 11/2008 | Salfi | A61B 8/488 600/454 |
| 2009/0005647 | A1* | 1/2009 | Bozdag | A61B 1/31 600/235 |
| 2009/0198102 | A1* | 8/2009 | Chen | A61B 1/00105 600/114 |
| 2009/0259110 | A1* | 10/2009 | Bastia | A61B 1/31 600/235 |
| 2010/0041954 | A1* | 2/2010 | Bastia | A61B 1/32 600/210 |
| 2010/0182569 | A1* | 7/2010 | Artsyukhovich | A61B 1/0661 351/221 |
| 2010/0234859 | A1* | 9/2010 | Bastia | A61B 17/12013 606/140 |
| 2010/0280523 | A1* | 11/2010 | Chen | A61B 1/31 606/110 |
| 2010/0331620 | A1* | 12/2010 | Sohn | A61B 1/00006 600/104 |
| 2011/0201895 | A1* | 8/2011 | Bastia | A61B 1/31 600/219 |
| 2012/0016204 | A1* | 1/2012 | Bastia | A61B 1/00108 600/245 |
| 2013/0197313 | A1* | 8/2013 | Wan | A61B 1/32 600/202 |
| 2018/0146849 | A1* | 5/2018 | Bastia | A61B 1/042 |

* cited by examiner

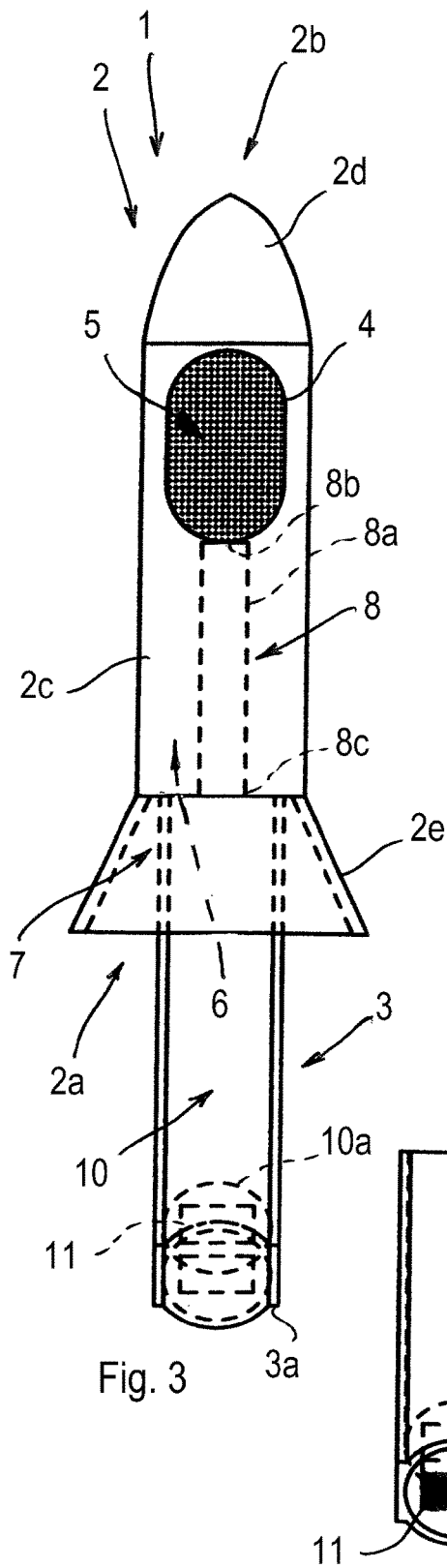
Fig. 3
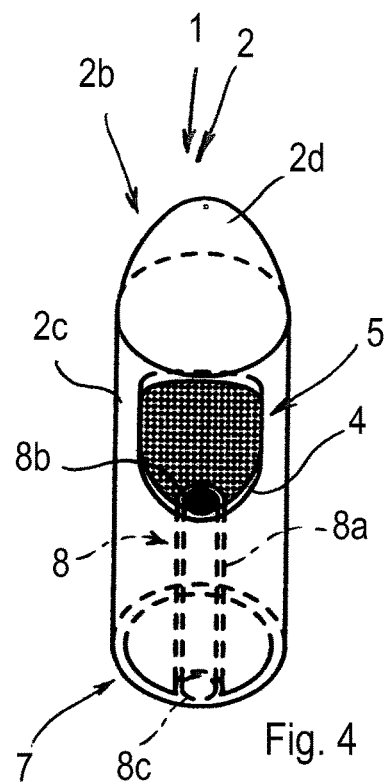
Fig. 4
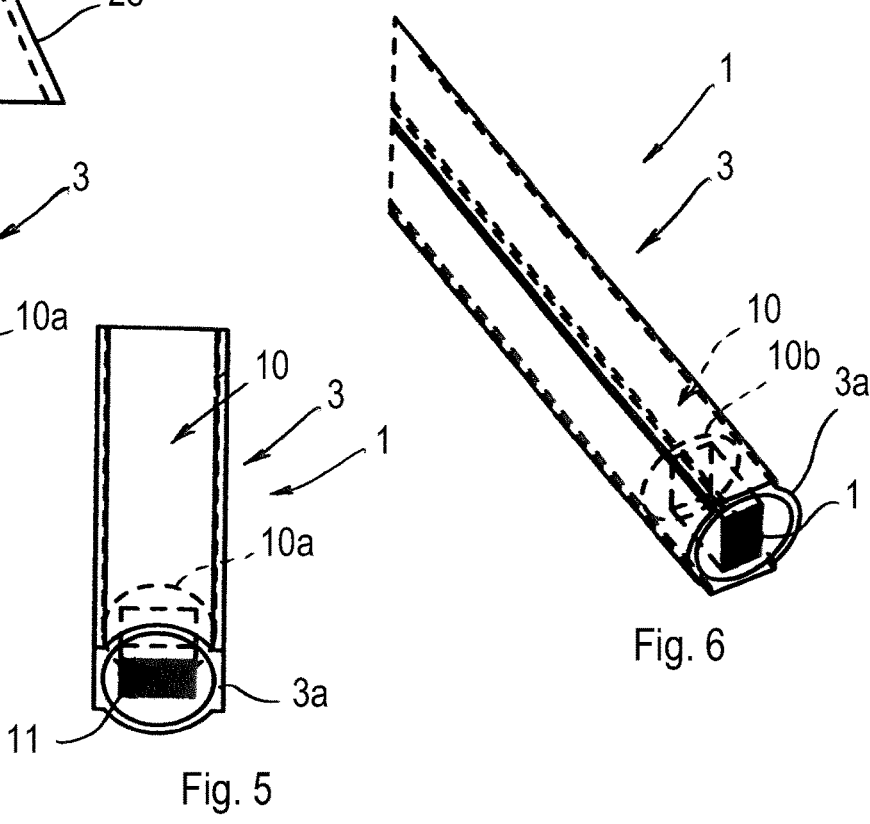
Fig. 5
Fig. 6

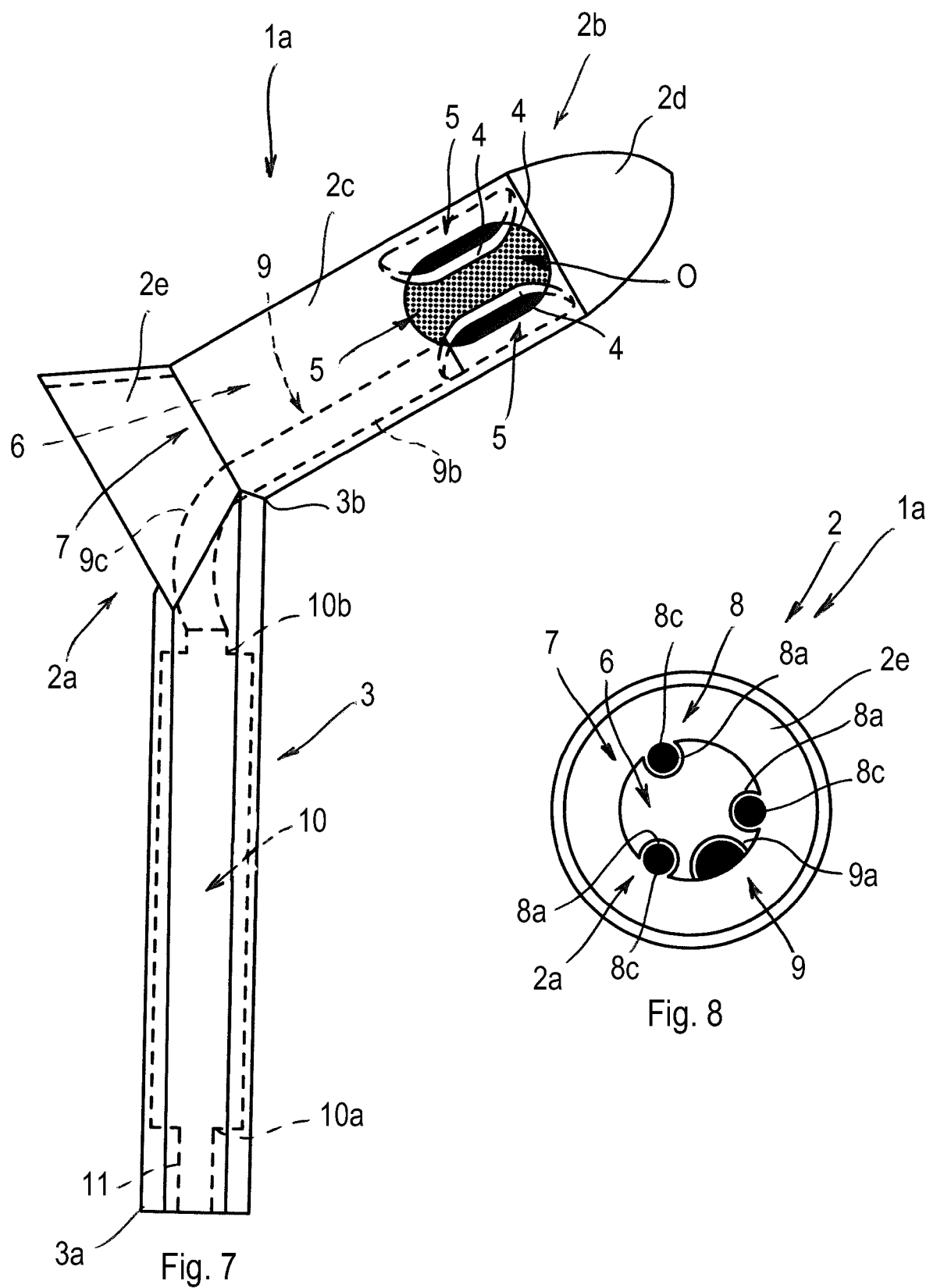

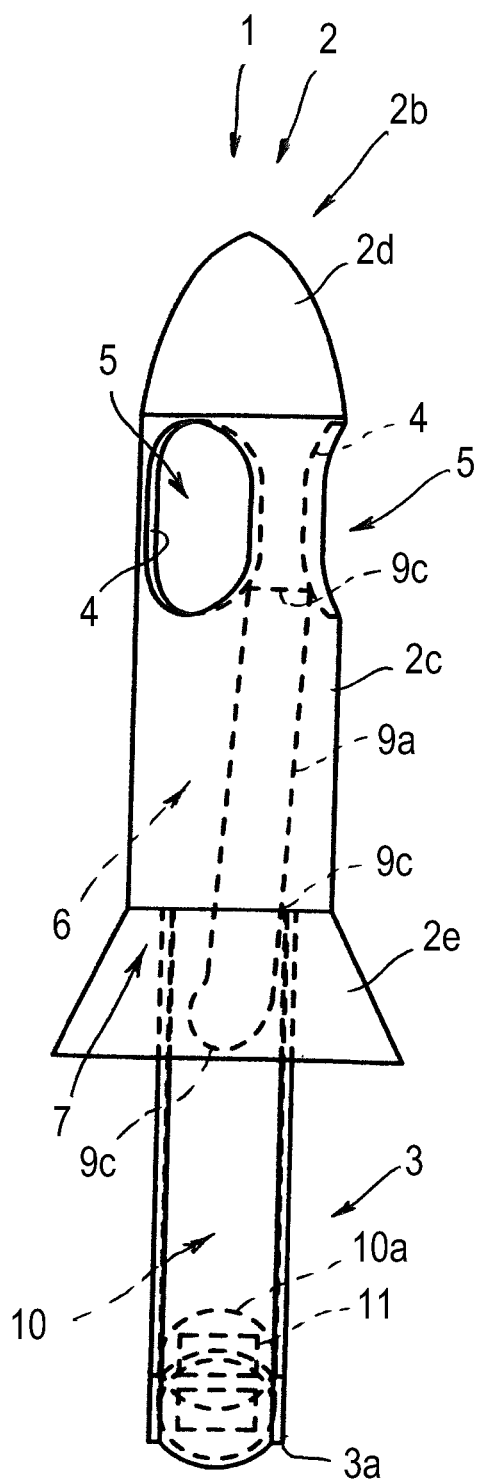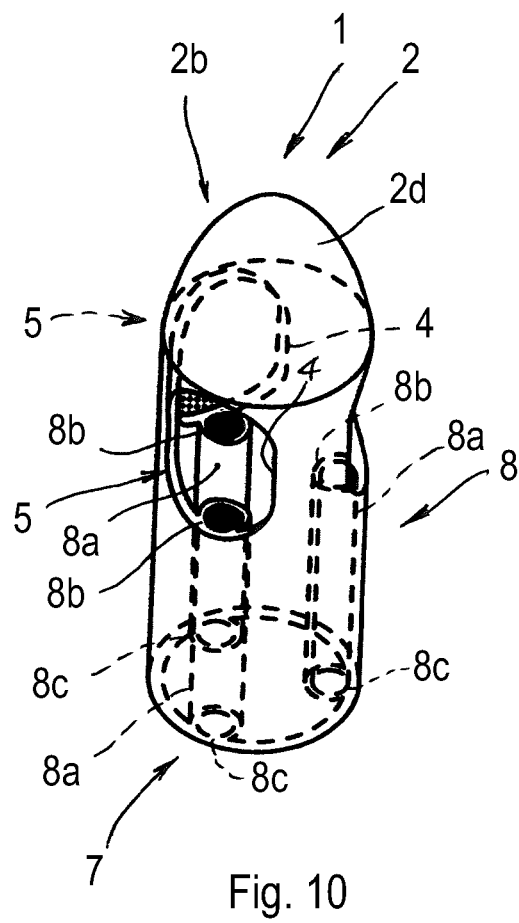
Fig. 9
Fig. 10

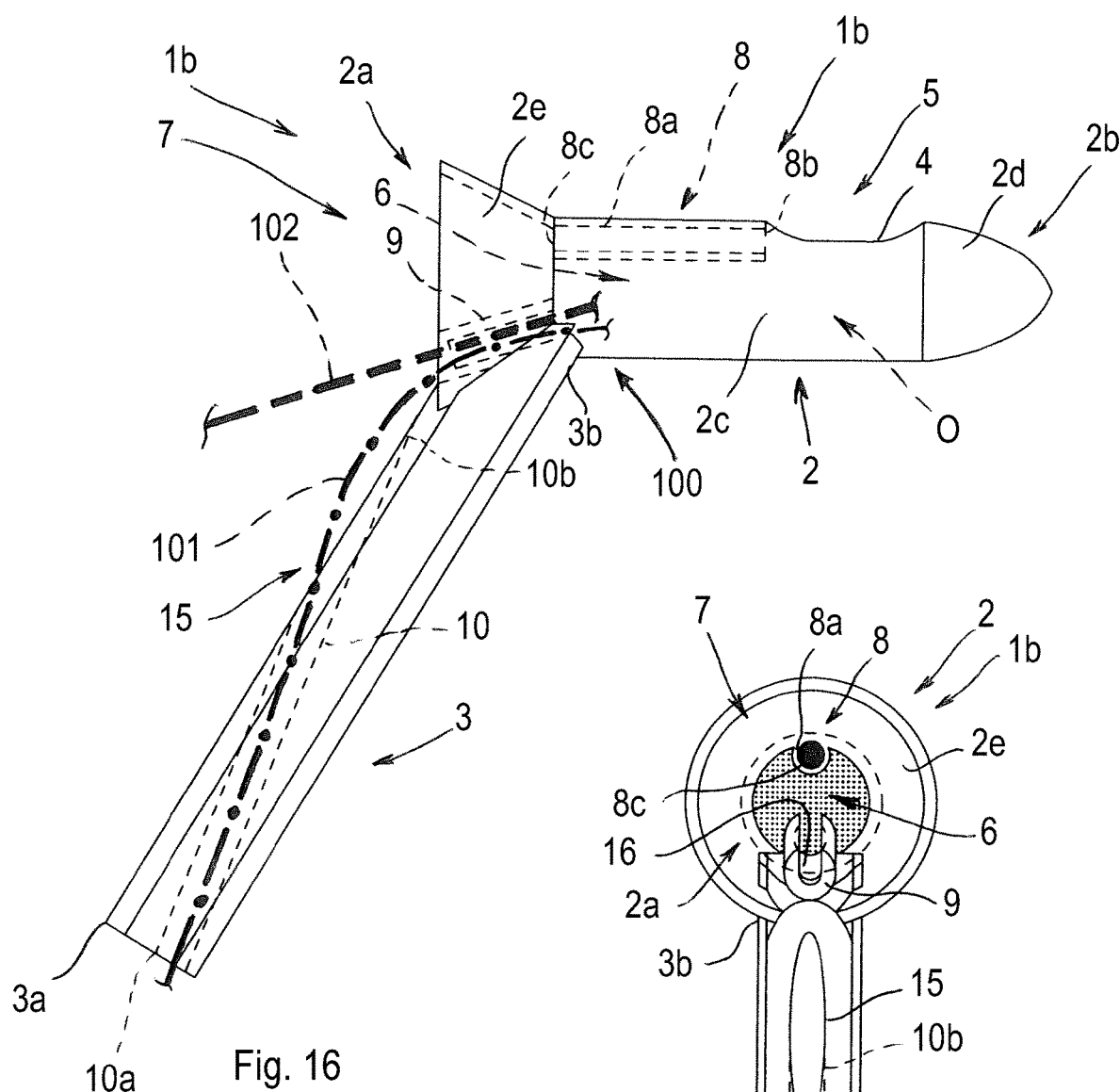
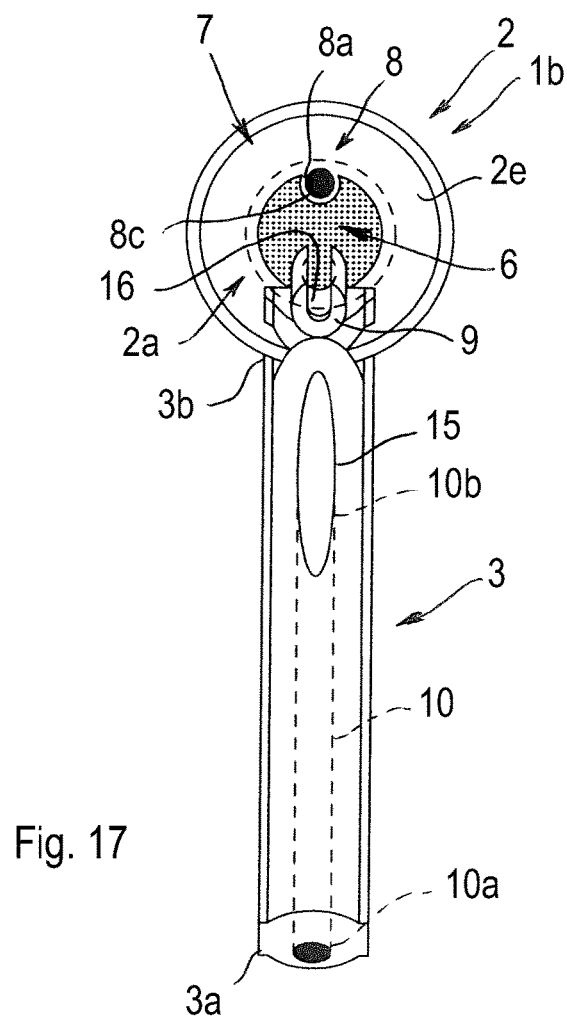
Fig. 16
Fig. 17

ANOSCOPE

FIELD OF THE INVENTION

The present invention relates to an anoscope, usable in the proctological field for surgical interventions, and to a method for the treatment of hemorrhoids, which can be implemented through the aforesaid anoscope.

BACKGROUND OF THE INVENTION

Anoscopes are known that comprise a cylindrical or a cylindrical-conical body, which body is provided with a handle that can be handled by an operator and which can be inserted, through the anal opening, in the terminal tract of the rectum of a patient. The body of the anoscope is hollow, it is opened at the opposite sides and arranged for receiving a dilator. The dilator is cylinder-shaped, it has an ogival or rounded distal end protruding outwardly from the distal end of the body of the anoscope and it acts (when the anoscope is inserted in the rectum) by stretching the muscular wall of the rectum without damaging the mucosa of the latter. In use, after inserting the anoscope, the dilator is extracted and the body remains in place, thus dilating temporarily the lumen of the terminal tract of the rectum and allowing to insert suitable instruments (hemorrhoidal ligators, suture needles-holders, clamps, etc.) to carry out diagnostic and/or surgical manoeuvres. According to the type of anoscope, the portion of intestinal mucosa to be examined and/or treated surgically is made accessible to the operator (surgeon) through the distal end of the body (which can have a truncated end or be bevelled) or through one or more so called operating windows, namely incisions obtained on the side wall of the body.

A drawback of the above disclosed anoscopes is that, in order to light effectively the operating field, namely the zone of rectal mucosa to be treated surgically (for example to occlude an arterial branch afferent to a hemorrhoid), it is necessary to use a suitable lighting device. The latter can for example be a flexible cable made of optical fibre associated to an external source of light. Therefore, the operator has to remove the dilator from the body of the anoscope and insert the lighting device inside the cavity of the latter. Once inserted, the lighting device has to remain in place (namely, inside the cavity of the body of the anoscope) substantially for all the time necessary to complete the surgical intervention. However, the encumbrance inevitably produced by the lighting device substantially interferes with the actions to be performed in the operating field, making it more uncomfortable for the operator to carry out the intervention. In addition, the intervention time tends to protract, as the operator must prearrange a suitable lighting of the operating field before starting the intervention, and this makes the execution of the intervention more uncomfortable for the patient too.

A further drawback of the above disclosed anoscopes is found when the operator must use a surgical instrument in the operating field. In this case, in fact, the operator is forced to position into the cavity of the anoscope, near the operating field, both the lighting device and the surgical instrument. Consequently, the accessibility of the operating field is significantly reduced due to the overall encumbrance produced by the surgical instrument and by the lighting device. Moreover, the operator is forced to manage manually a plurality of devices (anoscope, surgical instrument, lighting device) in a substantially contemporaneous manner. All this contributes to make it further uncomfortable to carry out a surgical intervention on the rectal mucosa of a patient.

A further and more general drawback of the above disclosed anoscopes is caused by the presence of the dilator. Although the latter is an essential component of the anoscope (since it enables the muscular wall of the rectum to be stretched without damaging the mucosa thereof), it is however an element which interferes with the accessibility of the operating field and which has to be removed, in use, by the operator in order to freely enter the inner cavity of the anoscope. However, in order to insert and extract the dilator, the operator is forced to carry out a number of manoeuvres substantially protracting the time of the surgical intervention, making the latter more complex for the operator and more uncomfortable for the patient.

The drawbacks connected to the methods that are ordinarily used to treat hemorrhoids in patients must be added to the above disclosed drawbacks that are related to the structure of known anoscopes. In the field of the proctological surgery, the treatment of hemorrhoids, namely of the hemorrhoidal disease, is usually carried out by removing the hemorrhoidal cushions or nodules (so called hemorrhoidectomy) or repositioning the hemorrhoidal nodules in the respective anatomic seat (so called hemorrhoidopexy). The hemorrhoidopexy, although being less bloody and invasive than hemorrhoidectomy, requires however to cut the patient's tissues. The hemorrhoidopexy in fact provides for a correction of the mucosal prolapse and a consequent repositioning of hemorrhoids by applying suturing stitches. The hemorrhoidopexy, like hemorrhoidectomy, causes post-operative pain and requires a post-operative control of the patient.

In the field of the proctological surgery, and in particular in the field of the surgical treatment of the hemorrhoidal disease, it is thus significantly perceived the need for instruments, in particular anoscopes, and methods to treat hemorrhoids in the patients enabling the various above disclosed prior art drawbacks to be overcome.

SUMMARY OF THE INVENTION

An object of the present invention is to improve the known anoscopes.

Another object is to make available an anoscope that enables the operating field to be lit suitably, avoiding at the same time the effect of encumbrance caused by the known lighting devices.

A further object is to make available an anoscope that enables a plurality of devices to be positioned near the operating field, keeping the latter freely accessible to an operator.

Another further object is to make available an anoscope that avoids an operator the need to manage manually, and substantially simultaneously, a plurality of devices during a surgical intervention carried out on the rectal mucosa.

Yet another object is to make available an anoscope that enables the muscular wall of the rectum to be stretched suitably without damaging the mucosa thereof, avoiding at the same time all the manoeuvres that are necessary to insert and extract the dilator.

Yet a further object is to make available a method for treating a hemorrhoid that avoids the arousal of post-operative pain in the treated patient and that also enables the need for a post-operative control of the treated patient to be avoided.

In a first aspect of the invention, an anoscope is provided, as defined in claim 1.

In a second aspect of the invention, a method for treating hemorrhoids is provided, as defined in claim 25.

Owing to these aspects, an anoscope enabling the operating field to be lit suitably, thus avoiding the need to use an auxiliary lighting source (external to the anoscope) and the effect of encumbrance that is obtained by inserting a prior art lighting device into the cavity of the anoscope, and a method for treating hemorrhoids, which avoids the arousal of postoperative pain in the treated patient and which further enables the need for a post-operative control of the treated patient to be avoided, are provided.

The anoscope according to the invention further enables a plurality of devices to be positioned near the operating field and at the same time to keep the operating field freely accessible to the operator. The aforesaid plurality of devices can be kept positioned correctly near the operating field without requiring a direct and constant manual intervention by the operator. As it will be hereinafter explained more in detail, this is made possible by the fact that the body of the anoscope according to the invention is internally provided with a seat and a housing, arranged for containing respectively a lighting device and at least one surgical instrument. Furthermore, the anoscope according to the invention enables the muscular wall of the rectum to be stretched suitably without damaging the mucosa thereof and avoiding the use of the dilator, which is made possible by the overall conformation of the anoscope.

As it will be hereinafter explained more in detail, the method according to the invention enables a localized heat to be produced in the rectal submucosa, namely a heat that is limited to the zone of rectal mucosa comprising the hemorrhoid. This localized heat at first has a decongestant effect and subsequently causes a localized cicatricial fibrosis. The method according to the invention can be implemented by using the anoscope according to the invention in combination with an electric scalpel or a radio frequency scalpel, provided with a monopolar (single active electrode) or bipolar (pair of active electrodes) active electrode, or by using the anoscope according to the invention in combination with an element for transporting laser light radiation—as for example an optical fibre cable—connected to a laser light radiation generator (so called laser scalpel).

BRIEF DESCRIPTION OF THE DRAWINGS

The invention will be better understood with reference to the attached drawings that show some exemplary and non-limiting embodiments thereof, in which:

FIG. 3 is a schematic plan and from above view of the anoscope of FIG. 1;

FIG. 4 is a schematic perspective and incomplete view, showing a part of the anoscope of FIG. 1;

FIG. 5 is a schematic incomplete, plan and from above view, showing a constructive detail of the anoscope of FIG. 1;

FIG. 6 is a schematic perspective and incomplete view of the constructive detail shown in FIG. 5;

FIG. 7 is a schematic side view, showing an alternative embodiment of the anoscope according to the invention;

FIG. 8 is a schematic, front and incomplete view, showing a proximal end of the anoscope of FIG. 7;

FIG. 9 is a schematic plan and from above view, of the anoscope of FIG. 7;

FIG. 10 is a schematic perspective and incomplete view, showing a part of the anoscope of FIG. 7;

FIG. 16 is a schematic side view of the anoscope of FIG. 12;

FIG. 17 is a schematic front view, showing the proximal part of the anoscope of FIG. 12;

DETAILED DESCRIPTION OF THE INVENTION

Figures 1, 2:
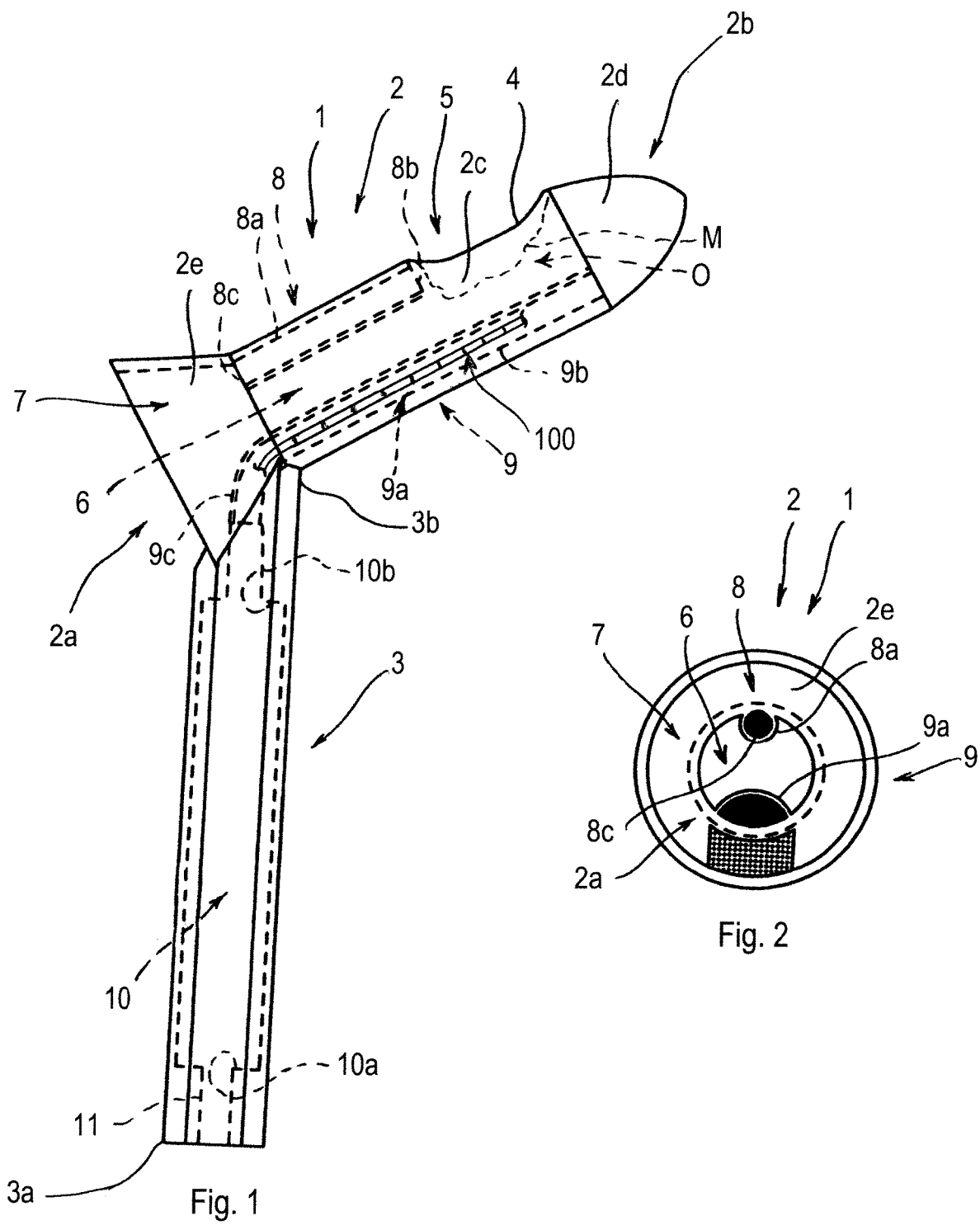
FIG. 1 is a schematic side view, showing an anoscope according to the invention.
FIG. 2 is a schematic incomplete view, showing a proximal end of the anoscope of FIG. 1.

In the present description, as well as in the enclosed claims, the adjective "proximal" defines a part, a segment or an end of the anoscope 1 which, in use, faces an operator (for example a surgeon) holding and/or using the anoscope. Consequently, the adjective "distal" defines a part, a segment or an end of the anoscope 1 that, in use, points to a direction opposite to the operator holding and/or using the anoscope. In the present description, as well as in the enclosed claims, the use of the term "hemorrhoid" in the singular is to be intended as "at least one hemorrhoid" and therefore does not exclude that the anoscope and/or the method according to the invention can be used effectively to treat a plurality of hemorrhoids in a same patient. In the present description, as well as in the enclosed claims, the terms "video endoscope", "endoscopic video camera", "endoscopic camera" and "endoscope" are used in an interchangeable manner, as well as the term "endoscope" includes both rigid and flexible endoscopes. In the present description, as well as in the enclosed claims, the terms "element for transporting laser light radiation connected to a laser light radiation generator" and "laser scalpel" are used in an interchangeable manner. In the present description, as well as in the enclosed claims, the terms "hemorrhoidal cushion" and "hemorrhoidal nodule" are used in an interchangeable manner. In the present description, as well as in the enclosed claims, the term "spot" means a period of repeated supply of electric power by an electric scalpel, or a period of repeated supply of laser light radiation by a laser scalpel.

FIGS. 1 to 6 show an anoscope 1, which is usable to treat surgically proctological pathologies, in particular hemorrhoids, and comprises a body 2 and a graspable portion 3. The body 2 is the part of the anoscope 1 that is arranged for being inserted (passing through the anus) into the terminal tract of the rectum of a patient, while the graspable portion 3 is arranged for being grasped by an operator, for example a surgeon. The anoscope 1 is made of a suitably sterilisable polymeric material, as for example polypropylene, or another material suitable for surgical use.

The body 2, which is approximately cylinder-shaped, comprises a proximal end 2a, to which the graspable portion 3 is fixed, and a distal end 2b. The proximal end 2a and the distal end 2b are mutually opposite. The body 2 comprises three segments, which are hollow and mutually connected: an intermediate segment 2c, which is approximately cylindrical and is provided with an external smooth surface; a distal segment 2d, which is approximately ogival or rounded and provided with an external smooth surface; a proximal segment 2e, which is approximately truncated cone-shaped. The distal segment 2d substantially corresponds to the distal end 2b, which is thus approximately ogival or rounded and provided with an external smooth surface. In the wall of the intermediate segment 2c, near the distal segment 2d—and thus near the distal end 2b—an incision 4 is made defining an operating window 5. More precisely, the operating window 5 is made near the distal end 2b, in a wall portion of the intermediate segment 2c that faces upwards when the anoscope 1 is grasped by the operator, namely when the body 2 of the anoscope 1 is positioned horizontally and the graspable portion 3 is arranged obliquely from the top to the bottom. Although the operating window 5 shown in the Figures has an outline that is approximately elliptical, not shown embodiments are also possible, in which the operating window has an approximately circular outline or an approximately quadrilateral outline. The intermediate segment 2c, the distal segment 2d and the proximal segment 2e define altogether a cavity 6. When the anoscope 1 is inserted in the terminal tract of the rectum of a patient, the cavity 6 communicates with the external environment through an inlet opening 7, which is circular and obtained in the proximal end 2a of the body 2, and with the intestinal lumen through the window inside the cavity 6 and, in particular, inside an operating field O. The latter corresponds to the zone of the cavity 6 which, in use, is partially occupied by the protruding portion of rectal mucosa M.

From what above disclosed and from the Figures (see in particular FIGS. 1, 3 and 4), it is clear the intermediate segment 2c and the distal segment 2d of the body 2 form altogether an element that can be compared to the dilator included in the known anoscopes. Therefore, in use, the body 2 acts both as a dilator, stretching the muscular wall of the rectum without damaging the mucosa thereof, and as an actual anoscope, defining an operating field within which the surgeon can reach the portion of rectal mucosa to operate on. In this way, the anoscope 1 enables the muscular wall of the rectum to be stretched suitably without damaging the mucosa thereof, preventing at the same time all the necessary manoeuvres to insert and extract the dilator.

In the cavity 6 of the anoscope 1 a seat 9, arranged for receiving a prior art lighting device 100 (schematically shown in FIG. 1), and a housing 8, arranged for receiving a surgical instrument 103 of known type (schematically shown in FIG. 19), are comprised. The surgical instrument can in particular be a monopolar or bipolar active electrode of electric scalpel or radio frequency scalpel, or an element for transporting laser light radiation—such as for example an optical fibre cable—connected to a laser light radiation generator (so called laser scalpel).

The housing 8 comprises a duct 8a, which is substantially shaped as a cylindrical tube and protrudes inside the cavity 6 from the wall of the intermediate segment 2c of the body 2. More exactly, the duct 8a protrudes from a zone of the wall of the intermediate segment 2c that faces the distal end 3b of the graspable portion 3. The duct 8a is substantially rectilinear and parallel to a longitudinal axis (not shown) of the body 2 and extends between the inlet opening 7 and the operating window 5 (FIG. 1; FIG. 3; FIG. 4). The duct 8a comprises a distal opening 8b and a proximal opening 8c, mutually opposite. It is possible to insert the surgical instrument 103 into the duct 8a through the proximal opening 8c. The surgical instrument can comprise for example a monopolar or bipolar active electrode of an electric scalpel or of a radio frequency scalpel, or an element for transporting laser light radiation, for example an optical fibre cable, connected to a generator of laser light radiation (so called laser scalpel). Through the distal opening 8b, a corresponding distal end of the active electrode can protrude outside the duct 8a and thus near the operating field O. In this way, the aforesaid end of the active electrode (or of any other suitable surgical instrument positioned inside the duct 8a) can come into contact with the portion of rectal mucosa M and easily penetrate through the latter.

The seat 9 comprises a tubular channel 9a, which has a transverse section that is approximately hemispherical and comprises a main segment 9b and a connecting segment 9c (mutually connected). The main segment 9b is rectilinear, parallel to the longitudinal axis of the body 2 and protrudes from a zone of the wall of the intermediate segment 2c that is adjacent to the distal end 3b of the graspable portion 3, namely from a zone of the wall of the intermediate segment 2c that faces the duct 8a (as shown in FIGS. 1 and 2). In other words, the duct 8a and the main segment 9b face each other inside the cavity 6. The main segment 9b extends between the inlet opening 7 and the distal segment 2d of the body 2, while the connecting segment 9c, that is curved, extends between the inlet opening 7 and the graspable portion 3 (within which it is partially contained). In the tubular channel 9a it is possible to insert a lighting device 100 of the known type, for example a strip of light emitting diodes (LEDs), through which it is possible to light suitably (in use) the cavity 6, in particular the operating field O, inside the anoscope 1. The lighting device 100 is shown schematically in FIG. 1.

It should be noted that the lighting device 100 can be associated to, or comprised in, a prior art image acquiring device. In particular, the lighting device 100 can be the distal end of a prior art image acquiring device, such as an endoscope for diagnostic and/or surgical use. Typically, an endoscope comprises a proximal end, which can be connected to an external light source (for example, LED, halogen or Xenon lamps), and a distal end, which is inserted into the body cavity of the patient. The light produced by the external light source is transmitted from the proximal end to the distal end (through a system of lens or through a bundle of optical fibres) and exits from the distal end, so as to light the inner body cavity.

For a skilled in the art person, it is thus clear that the distal end of a prior art image acquiring device (such as an endoscope) can be used as a lighting device and that the lighting device 100 can therefore be associated to, or comprised in, a prior art image acquiring device. For this purpose, an embodiment of the anoscope according to the invention will be hereinafter disclosed (with reference to FIGS. 12 to 15) that can be used in combination with a prior art image acquiring device, such as for example an endoscope.

The lighting device 100 can be of such a length as to occupy the cavity of the connecting segment 9c and the cavity of the main segment 9b, or it can be of such a length as to occupy only the cavity of the main segment 9b. In this second case, the connecting segment 9b is intended for housing only a power cord of the lighting device 100. In the case of a lighting device 100 consisting of light emitting diodes, the power cord is used to supply the aforesaid diodes with a low tension electriccurrent, for example a 12 Volt electric current. In one embodiment that is not shown, the tubular channel 9a only consists of the main segment 9b (namely, the connecting segment 9c is missing). Consequently, in the aforesaid embodiment the lighting device 100 (or a corresponding power cord) is placed directly in contact with the external environment in a zone of the anoscope 1 comprised between the inlet opening 7 and the graspable portion 3. As the tubular channel 9a is intended for receiving the lighting device 100, both the main segment 9b and the connecting segment 9c are made of a suitably sterilisable transparent or partially transparent (translucent) polymeric material. In one embodiment that is not shown, the main segment 9b and/or the connecting segment 9c are made of a not transparent polymeric material and are thus provided with walls in which openings (e.g. holes) are obtained to allow the passage of the light.

From what above disclosed and from the Figures (in particular FIGS. 1 and 2), it is clear that, owing to the seat 9, the anoscope according to the invention enables the operating field O to be lit suitably, however avoiding the effect of encumbrance caused by the lighting devices in the known anoscopes. In fact, the seat 9 is made near the wall of the body 2 of the anoscope 1, which prevents the lighting device 100 from being accidentally displaced inside the cavity 6 during an intervention and from hindering the view of the operating field O, even only partially. It is similarly clear that, due to the housing 8, the operator can position correctly a surgical instrument near the operating field O avoiding accidental displacements of the instrument inside the cavity 6 during the intervention, as well as the effect of encumbrance that is found in the known anoscopes (since the housing 8 too is made near the wall of the body 2 of the anoscope 1). In particular, the simultaneous presence of the housing 8 and of the seat 9 allows an operator to position a plurality of devices near the operating field O, however keeping the operating field O freely accessible during the intervention. This is achieved owing to the position of the housing 8 and of the seat 9, which are positioned near opposite zones of the cavity 6. More exactly, the housing 8 and the seat 9 are so positioned as to face each other (FIG. 2). In this way, during an intervention, despite the simultaneous presence of a surgical instrument and of a lighting device 100 in the cavity 6, a large zone of the latter can be freely acceded by the operator. Furthermore, as the surgical instrument and the lighting device 100 are kept in a suitable operative position by the housing 8 and the seat 9, the operator is not forced to manage manually, and substantially simultaneously, a plurality of devices during a surgical intervention carried out on the rectal mucosa.

The graspable portion 3 has a shape that is intermediate between the shape of a cylinder and the shape of a parallelepipedon (including in fact a pair of opposite flat side walls and a pair of opposite convex walls) and comprises a proximal end 3a and a distal end 3b, which are mutually opposite. While the proximal end 3a is free, the distal end 3b is fixed to the proximal end 2a of the body 2 in such a way that the graspable portion 3 is arranged transversally to the body 2 (FIG. 1). In embodiments that are not shown, the graspable portion 3 is cylinder- or parallelepipedon-shaped. Inside the graspable portion 3 a chamber 10 is obtained, which is arranged for receiving the lighting device 100. The chamber 10, which is approximately cylindrical and which extends along almost the whole length of the graspable portion 3, comprises an inlet end 10a, which is open and arranged near the proximal end 3a, and an outlet end 10b, which is open and arranged near the distal end 3b. Through the inlet end 10a, the lighting device 100 can be inserted and positioned inside the chamber 10. Through the outlet end 10b, the lighting device 100 can exit out of the chamber 10 and enter the seat 9 of the body 2, namely into the connecting segment 9c. Inside the graspable portion 3, between the proximal end 3a and the inlet end 10a, an electric connector 11 of known type is placed (schematically shown as a parallelepiped in FIGS. 5 and 6) that is arranged for receiving an electric power cord (not shown) of the known type and enabling the lighting device 100 to be electrically supplied. In one embodiment that is not shown, the lighting device 100 is completely contained inside the seat 9 and the chamber 10 only contains a power cord. In another embodiment that is not shown, the lighting device 100 is supplied by an electric supply battery of the known type, which is housed inside the chamber 10.

Although the anoscope 1 disclosed with reference to FIGS. 1-6 is provided with one operating window 5 only and with a housing 8 comprising a single duct 8a, alternative embodiments including more than one operating window 5 are possible. An exemplary but non-limiting embodiment of the anoscope according to the invention, including three operating windows and three ducts 8a, is described hereinafter.

FIGS. 7 to 10 show an anoscope 1a, which (similarly to the above disclosed anoscope 1) is usable to treat surgically proctological diseases, in particular hemorrhoids, and comprises a body 2 and a graspable portion 3. In FIGS. 7 to 10, all the elements of the anoscope 1a having the same structure and function as corresponding elements of the anoscope 1 are indicated by the same reference numbers. Only the differences between the anoscope 1 and the anoscope 1a will be described in detail in the following, thus omitting to disclose all the elements that are structurally and functionally equal in the two embodiments of the anoscope according to the invention. However, it is clear that also the housing 8 of the anoscopela can receive the surgical instrument 103 suitable to treat a hemorrhoid, as for example the monopolar or bipolar active electrode of an electric scalpel or of a radio frequency scalpel, or the element for transporting laser light radiation of a laser scalpel.

In the intermediate segment 2c of the body 2 of the anoscope 1a, near the distal segment 2d, three incisions 4 are made that define three operating windows 5. The three operating windows 5 are made in the intermediate segment 2c so as to be angularly staggered among each other (FIG. 7). In particular, the three operating windows 5 can be staggered of 120°. Although in FIGS. 7, 9 and 10 each of the three operating windows 5 has an approximately elliptical outline, not shown embodiments are also possible in which the operating windows have an approximately circular outline or an approximately quadrilateral outline.

The housing 8 of the anoscope 1a comprises three ducts 8a, each of which is substantially shaped as a cylindrical tube and protrudes inside the cavity 6 from the wall of the intermediate segment 2c of the body 2. As shown in FIG. 10, each duct 8a is parallel to the longitudinal axis (that is not shown) of the body 2 and is substantially aligned to the corresponding operating window 5. Therefore, the three ducts 8a are angularly staggered among each other and, in particular, can be staggered of 120°. Each duct 8a extends between the inlet opening 7 and the corresponding operating window 5.

Each duct 8a comprises the distal opening 8b and the proximal opening 8c, mutually opposite. Therefore, through the corresponding proximal opening 8c, in each duct 8a it is possible to insert a suitable surgical instrument. A distal opening of the latter can thus protrude (through the distal opening 8b) outside the duct 8a, namely near the operating field O.

The seat 9 comprises the tubular channel 9a, whose transverse section has an area that is lesser than the area of the transverse section of the tubular channel 9a of the anoscope 1 (as it can be seen by comparing FIG. 2 with FIG. 8). This is due to the fact that, in the anoscope 1a, the tubular channel 9a is placed between two ducts 8a (FIG. 8). Moreover, since three operating windows 5 are present, the main segment 9b does not extend until the distal segment 2d of the body 2 but ends near the operating windows 5.

By properly changing the position and/or the dimensions of the housing 8 and of the seat 9 (according to modalities that are clear for a skilled in the art person) it is possible to make embodiments (that are not shown) of the anoscope according to the invention including two or four operating windows 5.

Figure 11:
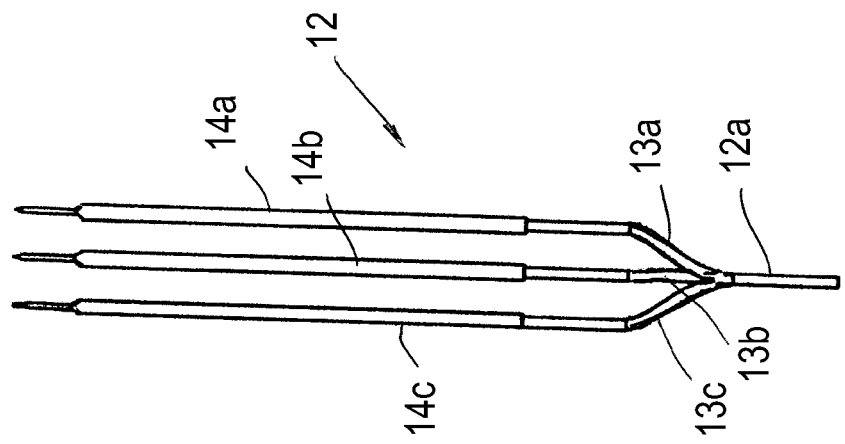
FIG. 11 is a schematic side view of a surgical instrument usable in combination with the anoscope of FIGS. 7-9.
Figure 13:
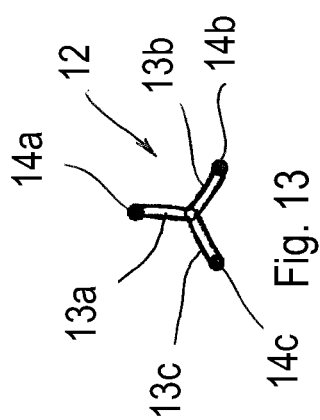
FIG. 13 is a schematic view of the distal end of the surgical instrument of FIG. 11.
Figure 12:
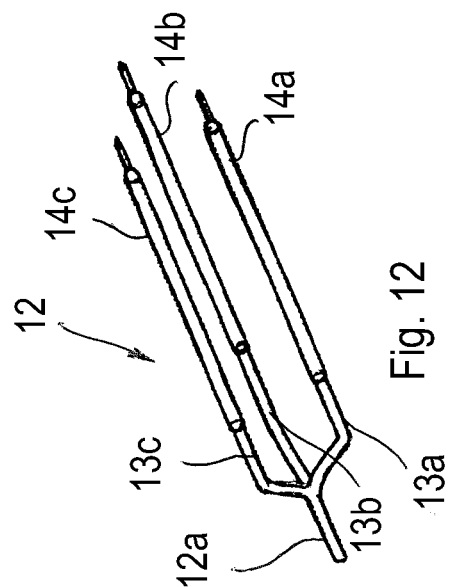
FIG. 12 is a schematic perspective view of the surgical instrument of FIG. 11.

FIGS. 11 to 13 show a surgical instrument, namely a multiple active electrode 12 that can be incorporated in, and can be electrically connected to, an electric scalpel or a radio frequency scalpel of the known type. The multiple electrode 12 includes three terminal elements (or tips) 14a, 14b, 14c and can be used effectively in combination with the anoscope 1a provided with three operating windows 5. More exactly, the multiple electrode 1 includes a main body 12a, which is substantially shaped as a cylindrical rod, from a distal end of which three branches 13a, 13b, 13c (each of which is shaped substantially as a cylindrical rod) lead. The three branches 13a, 13b, 13c are angularly staggered among each other, in a same manner as the three operating windows 5 of the anoscope 1a (with which the multiple electrode 12 is used) are angularly staggered among each other. Therefore, according to the configuration of the three operating windows 5 in the anoscope 1a, the three branches 13a, 13b, 13c can be staggered of 120° (as shown in FIG. 13) or can be staggered of angles that are higher or lower than 120° (in embodiments that are not shown). From each branch 13a, 13b, 13c a corresponding terminal element, or tip, 14a, 14b, 14c, leads. Each terminal element, or tip, 14a, 14b, 14c is substantially shaped as a cylindrical rod and corresponds (structurally and functionally) to a single active electrode of electric scalpel of the known type.

Moreover, each terminal element, or tip, 14a, 14b, 14c is of such a length as to completely occupy a corresponding duct 8a and to protrude outside the corresponding distal opening 8b, so as to easily reach the operating field O of the anoscope 1a.

Owing to the multiple electrode 12, instead of inserting (and electrically supplying) the active electrodes of three distinct surgical instruments (three electric scalpels) in the three ducts 8a of the anoscope 1a, it is possible to use more simply a single multiple electrode 12 of a single electric scalpel.

Using the anoscope 1 (or 1a) an operator can effectively reach and treat surgically a hemorrhoid, according to a general procedure hereinafter disclosed. In use, the operator grasps the graspable portion 3 of the anoscope 1 and points the anoscope 1 so that the graspable portion 3 is parallel to the intergluteal sulcus of the patient and the distal end 2d of the body 2 is positioned near the anus opening of the patient. The anoscope 1 can thus be easily inserted into the terminal tract of the rectum. This is made possible by the external shape of the body 2 (and in particular of the external shape of the distal end 2d), which enables the intestinal lumen to be dilated and the intestinal mucosa to be stretched. In this way, the operator can bring the intermediate segment 2c of the body 2—and thus the operating window 5—at the level of the hemorrhoid to be treated. The latter protrudes through the operating window 5 within the operating field O, suitably lit by the lighting device 100 housed in the tubular channel 9a, and can be treated surgically by operating a surgical instrument—for example a monopolar or bipolar active electrode of electric scalpel or of radio frequency scalpel—housed in the duct 8a and protruding from the latter (through the distal opening 8b) in the operating field O.

If the anoscope 1a is used, the presence of three operating windows 5 enables the operator to surgically treat up to three hemorrhoids on a same patient during a single intervention. This can be done by using in combination with the anoscope 1a, e.g. three electrodes of three different electric scalpels, or a single electric scalpel provided with the multiple electrode 12.

FIGS. 14 to 17 show an anoscope 1a, that (similarly to the above disclosed anoscope 1 and anoscope 1a) is usable to treat surgically proctological diseases, in particular hemorrhoids, and comprises a body 2 and a graspable portion 3. In FIGS. 14 to 17, all the elements of the anoscope 1b having the same structure and function as corresponding elements of the anoscope 1 are indicated by the same reference numbers. Only the differences between the anoscope 1 and the anoscope 1b will be described in detail hereinafter, thus omitting to disclose all the elements that are structurally and functionally equal in the two anoscopes according to the invention (anoscope 1 and anoscope 1b). However, it is clear that also the housing 8 of the anoscope 1b can receive the surgical instrument 103 suitable to treat a hemorrhoid, such as for example the monopolar or bipolar active electrode of an electric scalpel or of a radio frequency scalpel, or the element for transporting a laser light radiation of a laser scalpel.

The anoscope 1b differs from the anoscope 1 (disclosed with reference to FIGS. 1 to 5) with regard to the structure of the seat 9 and the chamber 10. The seat 9 is rectilinear, it extends longitudinally between the inlet opening 7 and the graspable portion 3 and is thus positioned outside the body 2 of the anoscope 1b. A longitudinal axis (that is not shown) of the seat 9 is arranged obliquely to the body 2, so that the seat 9 is inclined with respect to the body 2 when the body 2 is positioned horizontally (FIG. 16). The seat 9 has a transverse section which is substantially U-shaped and consequently is concave (FIG. 14; FIG. 17). The concavity of the seat 9 points to the opposite direction with respect to the graspable portion 3, namely the concavity of the seat 9 points upwardly when the body 2 is arranged horizontally. Therefore, the seat 9 of the anoscope 1b is made as a grooved element that is provided with a longitudinal groove 16 (FIG. 14; FIG. 17). As disclosed in detail hereinafter, the longitudinal groove 16 is able to house the lighting device 100.

Figures 14, 15:
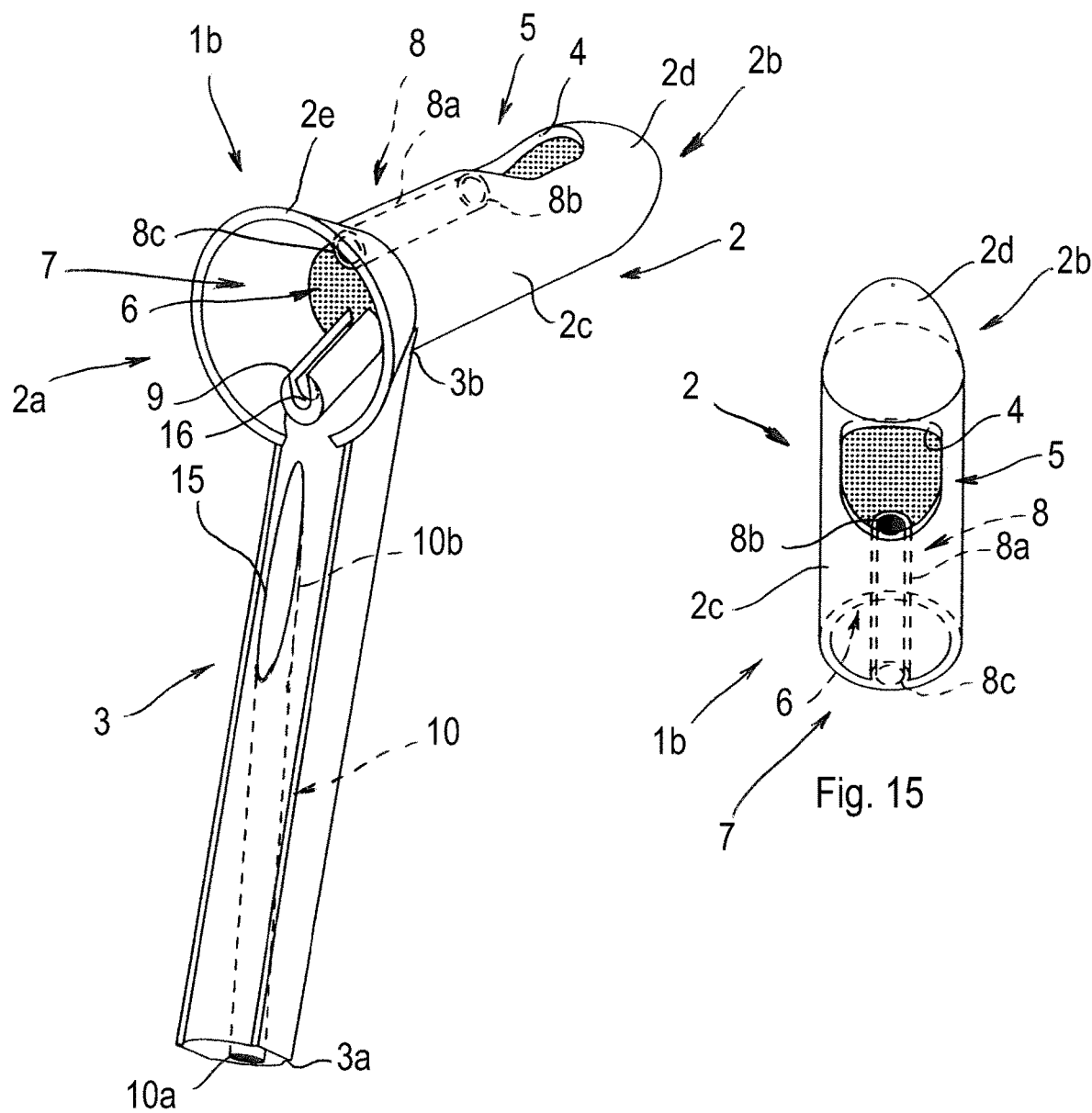
FIG. 14 is a schematic perspective view of another alternative embodiment of the anoscope according to the invention.
FIG. 15 is a schematic perspective and incomplete view, showing a part of the anoscope of FIG. 12.

The chamber 10 is shaped as a cylindrical tube and extends for almost all the length of the graspable portion 3 of the anoscope 1. A longitudinal axis (that is not shown) of the chamber 10 is arranged obliquely to the graspable portion 3, in such a way that the chamber 10 extends inside the graspable portion 3 not parallely to the latter (FIG. 16). As a result of this configuration, the outlet end 10b is not positioned near the distal end 3h (as in the case of the chamber 10 of the anoscope 1) and opens outside the graspable portion 3 with an outlet opening 15. The outlet opening 15 is approximately elliptical and extends near the seat 9 (FIG. 14). As disclosed in detail hereinafter, the chamber 10 is able to house a portion (in particular a flexible tubular portion) of the lighting device 100.

Although the anoscope 1b shown in FIGS. 14-17 is provided with a single operating window 5, by properly changing the position and/or the dimensions of the housing 8 and the seat 9 (according to modalities that are clear for a skilled in the art person) it is possible to make embodiments (that are not shown) of the anoscope according to the invention including two, three or four operating windows 5.

The anoscope 1b can be used in combination with a lighting device 100 associated to, or comprised in, an image acquiring device of the known type. In particular, the lighting device 100 can comprise the distal end of an image acquiring device of the known type, such as an endoscope for diagnostic and/or surgical use. In particular, the endoscope can be a video endoscope, namely an electronic endoscope whose proximal end includes a terminal sensor. Once inserted in a body cavity of a patient, the terminal sensor generates video signals and sends the latter to a computerized processor. The computerized processor processes the video signals, transforms them into images and transfers them to a displaying device of the known type, e.g. a monitor.

FIG. 16 exemplifies the way in which a lighting device 100, comprising the distal end of a flexible endoscope 101 (schematically shown by a dash-dot line) or the distal end of a rigid endoscope 102 (schematically shown with a dotted line) can be housed inside the seat 9 of the anoscope 1b.

The flexible endoscope 101—in particular the flexible tubular portion of the endoscope 101, containing a bundle of optical fibres—is first inserted in the chamber 10 through the inlet end 10a. Then, through the outlet opening 15 of the outlet end 10h, the flexible endoscope 101 can exit out of the chamber 10 and be inserted and caused to slide into the longitudinal groove 16 of the seat 9. In this way, the distal end of the flexible endoscope 101 can be positioned towards the operating field O and a beam of light (emitted, in use, by the distal end of the endoscope) can light the operating field O.

The rigid endoscope 102 can be inserted and caused to slide into the longitudinal groove 16 of the seat 9, so as to position the distal end of the rigid endoscope 102 towards the operating field and enable a beam of light (emitted, in use, by the distal end of the endoscope) to light the operating field O.

Figure 18:
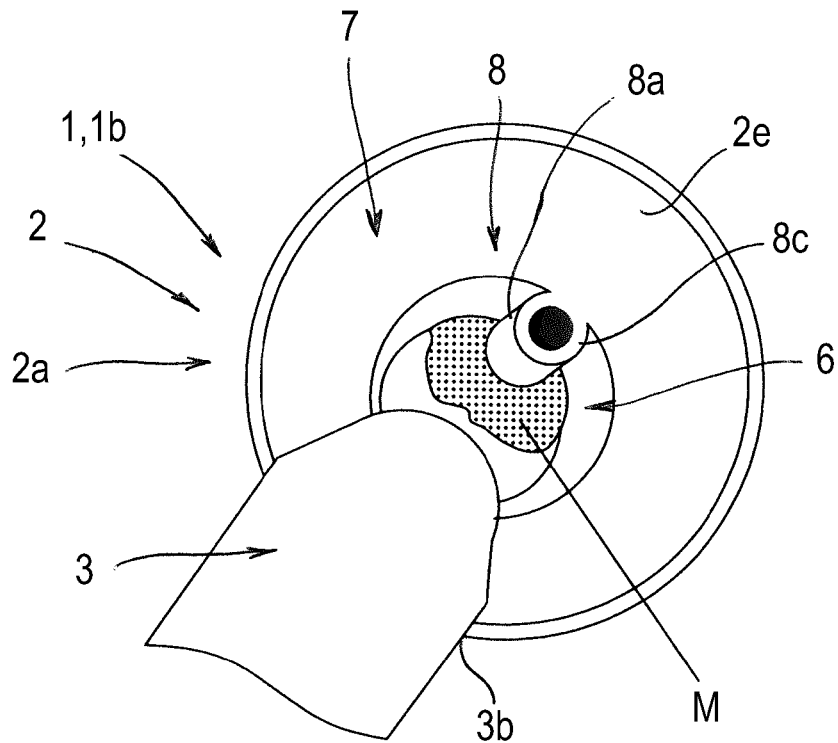
FIG. 18 is a schematic, fragmentary and incomplete view, showing the proximal end of the anoscope of FIG. 15 in a step of the method according to the invention.
Figure 19:
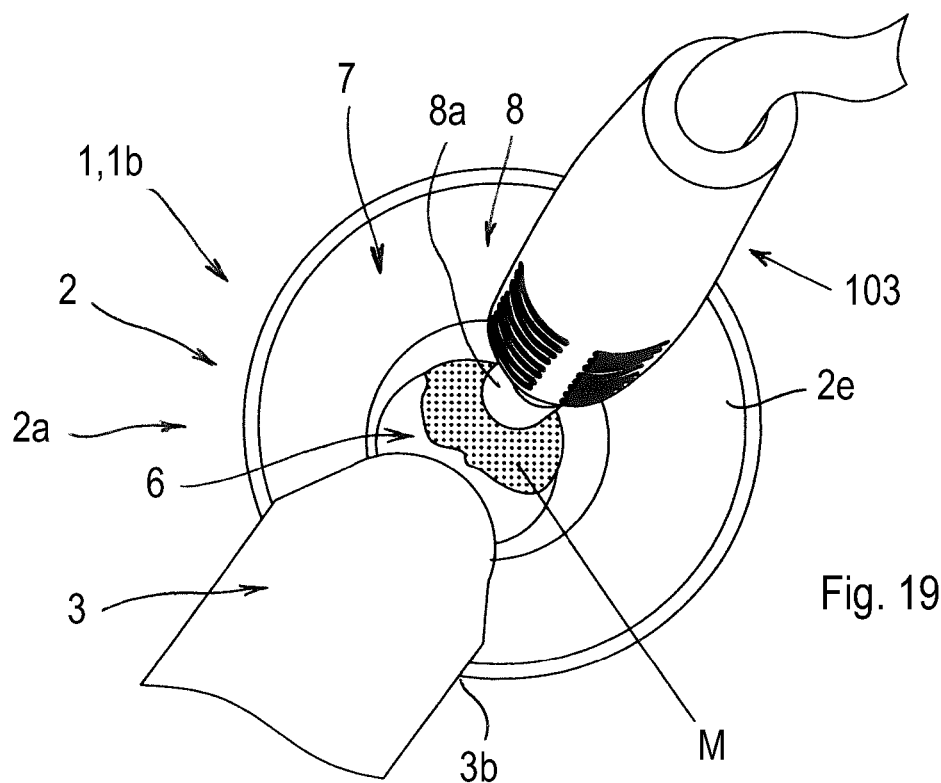
FIG. 19 is a schematic, fragmentary and incomplete view, showing the proximal end of the anoscope of FIG. 1 in a further step of the method according to the invention.

FIGS. 18 and 19 show in a schematic, exemplary and non-limiting manner, two steps of the method according to the invention, which enables a hemorrhoid to be effectively treated on a patient. The method according to the invention can be performed by using the anoscope according to the invention (or an anoscope of the known type). A general procedure for the use of the anoscope according to the invention has been previously disclosed.

The method according to the invention (called by the Applicant "submucosal thermal hemorrhoidopexy") is based on the possibility (experimentally verified by the Applicant) to produce a localized heat in the rectal submucosa, namely a heat that is limited to the zone of rectal mucosa comprising or overlying the hemorrhoid to be treated surgically. In particular, the method provides for treating a hemorrhoid by subjecting a portion of tunica submucosa proximal to the pectinate line (ideal line that separates the rectum from the anus and is defined by the anal papillae) to a thermal treatment. The heat necessary for the treatment is produced by an electric scalpel or by a radio frequency scalpel, provided by a monopolar or bipolar active electrode, or by a laser scalpel.

The principle of the method according to the invention is the induction of a rapid and selective tissue heating through the use of high frequency energy. When this high frequency energy is released in the zone of submucosa to be treated, a ionic agitation is induced in the biological tissues surrounding the tip of the surgical instrument (for example, an active electrode of an electric scalpel) and in this way heat is generated. It should be noted that, in the method according to the invention, the tissues adjacent to the electrode heat up rather than the electrode itself. Moreover, since energy at low potency level is used to heat tissues, a controlled increase of the temperature comprised between 50° C. and 100° C. is induced, thus avoiding undesired phenomena of tissues carbonization.

From a physiological point of view, first of all a protein denaturation occurs that causes a tissue coagulation and a consequent volume reduction. This volume reduction is an immediate and easily visible consequence of the heat treatment carried out. After about 10 days from the treatment date, the lesion is surrounded by fibroblasts of the connective tissue that replace the necrotic area as the result of an ordinary tissue reparation process. After about 2-3 weeks from the treatment date, the lesion is replaced by cicatricial tissue (cicatricial fibrosis), having a smaller volume than the original (hemorrhoidal) tissue. As time passes, the physiological process of partial reabsorption of the cicatricial tissue causes a further volume reduction and an enduring fixation of the (rectal) mucosa to the (rectal) muscular wall, which represents the desired therapeutical effect.

From a surgical point of view, the method according to the invention is implemented as hereinafter disclosed (in way of exemplary and non-limiting manner).

The patient to be treated is positioned in the so called Sims position (position wherein the patient lays on the left side, the left hip and the left lower limb are rectilinear, the right hip and the right knee are bent). The patient is thus sedated intravenously and submitted to local anaesthesia, if this is deemed necessary by the surgeon. An anoscope according to the invention (namely an anoscope 1, 1a or 1b), or an anoscope of the known type (having a truncated body, or a bevelled body, and a distal opening), is inserted into the terminal tract of the rectum of the patient through the anus. The body of the anoscope is positioned in such a way that the operating window 5 is near the zone of rectal mucosa to be treated. In particular, the operating window 5 can be positioned beyond the pectinate line, towards the rectum. In this position, the operating window 5 makes accessible a portion of the rectal mucosa corresponding to the proximal part of the corresponding hemorrhoidal cushion or nodule (left side hemorrhoidal nodule, right front hemorrhoidal nodule, right back hemorrhoidal nodule) or to the rectal mucosa interposed between the aforesaid nodules. Using the anoscope 1, 1a, 1b according to the invention, the rectal mucosa M will protrude through the operating window 5 (FIG. 18) within the anoscope (namely, within the operating field).

A suitable surgical instrument of the known type—for example an electric scalpel or a radio frequency scalpel, provided with a monopolar or bipolar active electrode, or the element for transporting the lighting radiation of a laser scalpel—can thus be positioned inside the body of the anoscope so as to reach the operating window 5 (or the distal opening) and, through the operating window 5 (or the distal opening), the zone of rectal mucosa to be treated.

By using the anoscope 1, 1a, 1b according to the invention, the surgical instrument 103 (for example a monopolar or bipolar active electrode of electric scalpel or radio frequency scalpel) is inserted in the housing 8 (FIG. 19) and a possible lighting device 100 (strip of light emitting diodes; rigid or flexible endoscope) is inserted in the seat 9.

The monopolar or bipolar active electrode of the electric scalpel is thus inserted into the rectal submucosa and operated, so as to dispense to the tissues a low intensity electric current, having a power comprised between 10 W and 30 W, by consecutive "spots" (repeated dispensing periods) of few seconds and having an average duration of 5 seconds, until a sufficient volume reduction of the zone of treated mucosa is achieved. This sequence of steps can be performed both using an electric scalpel or a radio frequency scalpel and using a laser scalpel.

The above disclosed sequence of steps can be performed and/or repeated in several zones of the rectal mucosa. In particular, the sequence of steps can be repeated in six different zones, namely at the level of each hemorrhoidal cushion or nodule (left side hemorrhoidal nodule, right front hemorrhoidal nodule, right back hemorrhoidal nodule) and in the three intermediate areas (zone comprised between left side hemorrhoidal nodule and right front hemorrhoidal nodule; zone comprised between left side hemorrhoidal nodule and right back hemorrhoidal nodule; zone comprised between right front hemorrhoidal nodule and right back hemorrhoidal nodule) in order to obtain an optimal fixation of the mucosa. As a further effect, the coagulation, and thus the occlusion, of the six terminal branches of the upper hemorrhoidal artery is achieved, thus carrying out (apart from the submucosal thermal hemorrhoidopexy) a dearterializing hemorrhoidopexy. Once the above disclosed sequence of steps is completed, it is possible to extract the surgical instrument from the submucosa and from the anoscope, then it is possible to remove the anoscope from the terminal tract of the rectum of the patient.

In brief, the method according to the invention (method for treating a hemorrhoid in a patient) comprises the following main steps:

a) Inserting an anoscope into the terminal tract of the rectum of a patient through the anal opening;
b) Positioning the body of the anoscope in such a way that one operating window or opening thereof is near a zone of rectal mucosa (which is in turn near the hemorrhoid) to be treated;
c) Positioning a surgical instrument suitable for treating hemorrhoids (for example: electric scalpel or radio frequency scalpel; laser scalpel) inside the body of the anoscope so as to reach the operating window or the distal opening and, through the latter, the zone of rectal mucosa to be treated.
d) Producing in the submucosa of the zone of rectal mucosa to be treated a localized heat (namely, a heat limited to the zone of rectal mucosal to be treated) through the surgical instrument;
e) Inducing a volume reduction of the hemorrhoid as a result of the aforesaid localized heat.

Through the production of localized heat in the aforesaid step d), a protein denaturation is induced in the zone of treated rectal mucosa (and thus in the hemorrhoid), followed by a tissue coagulation and a consequent, substantially immediate, volume reduction. After some time, a further volume reduction is achieved and permanently kept as a result of a cicatricial fibrosis, following from the localized heat treatment.

If the surgical instrument is the (monopolar or bipolar) active electrode of an electric scalpel or of a radio frequency scalpel, the method according to the invention also comprises the following step: inserting a distal end of the active electrode into the rectal submucosa and dispensing to the biological tissues a current of preset power, comprised between 10 W and 30 W, by consecutive "spots" (repeated dispensing periods) of few seconds and having an average duration of 5 seconds.

If the surgical instrument is an element for transporting laser light radiation—as for example an optical fibre cable—connected to a generator of laser light radiation (so called laser scalpel), the method according to the invention also comprises the following step: inserting a distal end of the element for transporting laser light radiation into the rectal submucosa and dispensing to the biological tissues a laser light radiation of preset power, comprised between 10 W and 30 W, by consecutive "spots" of preset duration and having an average duration of 5 seconds.

It should be noted that the results of the intervention are immediately visible and are enduring. Moreover, unlike the known surgical methods, the method according to the invention allows to substantially avoid the arousal of post-operation pain in the treated patient, as well as to avoid the need for a post-operation control of the treated patient. The method according to the invention can be implemented by using, interchangeably, the anoscope 1, the anoscope 1*a* or the anoscope 1*b* according to the invention.

From what above disclosed, it is clear that the anoscope and the method according to the invention can be effectively used in the proctological field and enable the (previously pointed out) drawbacks afflicting the prior art to be overcome effectively.

Variants and/or additions to what has been above disclosed and/or to what has been shown in the enclosed drawings are also possible. For example, the method according to the invention can be implemented by using an electric scalpel or a radio frequency scalpel, provided with monopolar or bipolar active electrode, or a laser scalpel in combination with an anoscope of the known type, having a truncated body or a bevelled body and a distal opening.

The invention claimed is:

1. Anoscope, comprising a graspable portion arranged for being grasped by an operator and a body arranged for being inserted into the terminal tract of the rectum of a patient, a cavity and at least one operating window being made in said body, said anoscope further comprising a housing arranged for containing at least one surgical instrument suitable for treating hemorrhoids and a seat arranged for containing at least one lighting device, said housing and said seat being comprised in said cavity, wherein said seat comprises a tubular channel or a grooved element and wherein said body comprises a proximal end and a distal end, wherein said graspable portion is fixed to said proximal end and wherein said proximal end has an inlet opening of said cavity, and Wherein said operating window is arranged nearer to said distal end than said proximal end, wherein said tubular channel comprises a main segment that extends between said inlet opening and a distal segment of said body.

2. Anoscope according to claim 1, wherein said housing and said seat are positioned inside said cavity so that they face each other.

3. Anoscope according to claim 1, wherein said distal end is ogival or rounded.

4. Anoscope according to claim 1, wherein said housing comprises at least one duct.

5. Anoscope according to claim 4, wherein said duct extends between said inlet opening and said operating window.

6. Anoscope according to claim 1, wherein said tubular channel further comprises a connecting segment, which is linked to said main segment and extends between said inlet opening and said graspable portion.

7. Anoscope according to claim 2, comprising a chamber arranged in said graspable portion, said chamber comprising an inlet end, which is open and arranged near a proximal end of said graspable portion, and an outlet end, which is open and arranged near a distal end of said graspable portion.

8. Anoscope according to claim 7, wherein said outlet end opens outside said graspable portion through an outlet opening.

9. Anoscope according to claim 6, wherein said tubular channel comprises a main segment, which extends between said inlet opening and a distal segment of said body, and a connecting segment, which is linked to said main segment and extends between said inlet opening and said graspable portion, said anoscope comprising a chamber arranged in said graspable portion, said chamber comprising an inlet end, which is open and arranged near a proximal end of said graspable portion, and an outlet end, which is open and arranged near a distal end of said graspable portion, wherein said chamber communicates with said connecting segment through said outlet end.

10. Anoscope according to claim 7, further comprising an electric connector that is positioned between said inlet end of said chamber and said proximal end of said graspable portion, said electric connector being arranged for receiving an electric power cord.

11. Anoscope according to claim 2, comprising, inside said housing, said surgical instrument suitable for treating hemorrhoids.

12. Anoscope according to claim 11, wherein said surgical instrument comprises a monopolar or bipolar active electrode of an electric scalpel, or a monopolar or bipolar active electrode of a radio frequency scalpel, or an element for transporting a laser light radiation of a laser scalpel.

13. Anoscope according to claim 1, including, inside said seat, said lighting device.

14. Anoscope according to claim 13, wherein said lighting device comprises a strip of light emitting diodes.

15. Anoscope according to claim 13, wherein said lighting device is associated to, or comprised in, an image acquiring device.

16. Anoscope according to claim 15, wherein said image acquiring device comprises an endoscope.

17. Anoscope according to claim 4, wherein three angularly staggered operating windows are provided in said body and wherein said housing comprises three ducts, said three ducts being aligned to said three operating windows and being angularly staggered.

18. Anoscope according to claim 17, comprising a multiple active electrode that is electrically connectable to an electric scalpel or to a radio frequency scalpel.

19. Anoscope according to claim 18, wherein said multiple electrode comprises three terminal elements, each of said terminal elements being received inside a corresponding duct.

20. Anoscope according to claim 19, wherein said multiple electrode comprises a main body, from a distal end of which three angularly staggered branches lead, said terminal elements leading from said branches.

\* \* \* \* \*